United States Patent [19]
Kolodny et al.

[11] Patent Number: 6,140,115
[45] Date of Patent: Oct. 31, 2000

[54] CANINE β-GALACTOSIDASE GENE AND GM1-GANGLIOSIDOSIS

[76] Inventors: Edwin H. Kolodny, 110 Bleecker St., #24 D, New York, N.Y. 10012-2106; Zhao-Hui Wang, 137-10 Franklin Ave., Apt. 301, Flushing, N.Y. 11355; Srinivasa Raghavan, 92 Princess Dr., North Brunswick, N.J. 08902; Baijin Zeng, 137-10 Franklin Ave., Apt. 301, Flushing, N.Y. 11355

[21] Appl. No.: 09/436,605

[22] Filed: Nov. 9, 1999

[51] Int. Cl.[7] .............................. C12N 15/12; C12N 9/38
[52] U.S. Cl. .................. 435/320.1; 435/183; 435/207; 435/6; 536/23.1; 536/23.2; 536/24.33
[58] Field of Search ..................................... 435/207, 183, 435/320.1, 6; 536/23.1, 23.2, 24.33

*Primary Examiner*—Rebecca E. Prouty
*Assistant Examiner*—Richard Hutson
*Attorney, Agent, or Firm*—Benjamin Aaron Adler

[57] ABSTRACT

The acid β-galactosidase cDNA of Portuguese Water (PW) dogs was isolated and sequenced. The entire encoding region of the gene consists of 2004 nucleotides coding a protein of 668 amino acids. Its encoding sequence indicates approximately 86.5% identity at the nucleotide level and about 81% identity at the amino acid level with the encoding region of the human acid β-galactosidase gene. The deduced amino acid sequence contains a 24-amino acid putative signal sequence, 6 possible glycosylation sites, and 7 cysteine residues. A homozygous recessive mutation, causing $G_{M1}$-gangliosidosis in PW dogs, was identified at nucleotide $G^{200} \rightarrow A$ in exon 2 resulting in an $Arg^{60} \rightarrow His$ (mutation R60H) amino acid substitution. The mutation creates a new restriction enzyme site for PmlI. Genotyping 115 dog samples for this acid β-galactosidase gene alteration readily distinguished affected homozygous recessive (n=5), heterozygous carriers (n=50), and normal homozygotes (n=60). DNA mutation analysis provided a method more specific than enzyme assay of β-galactosidase for determination of carriers.

6 Claims, 9 Drawing Sheets ggagggacgtggcgacggcgATGGCGCGGCCCGCGGCGGTTCGCGTGCT    50
                    M   A   R   P   A   A   V   R   V   L CTGGGCGCTGCTGCTGCCGCTGCTGCTGGGCTCTGCGCGCGGCCTGCGGA   100
 W   A   L   L   L   P   L   L   L   G   S   A   R   G   L   R   <u>N</u>

ATGCTTCCCAGAGGACATTCACAATTGACTACAGCCACAACCGCTTCCTG   150
 <u>A</u>   <u>S</u>   Q   R   T   F   T   I   D   Y   S   H   N   R   F   L

AAGGACGGCCAGCCCTTCCGCTACATTTCGGGAAGCATTCACTATTCCCG   200
 K   D   G   Q   P   F   R   Y   I   S   G   S   I   H   Y   S   R

CGTGCCCCGCTTCTACTGGAAGGACCGCCTGCTGAAGATGAAGATGGCTG   250
 V   P   R   F   Y   W   K   D   R   L   L   K   M   K   M   A

GGCTGAATGCCATCCAGACGTACGTGCCCTGGAACTTTCACGAACCCCAG   300
 G   L   N   A   I   Q   T   Y   V   P   W   N   F   H   E   P   Q

CCGGGACAGTACCAGTTTTCTGGGGAGCAGGATGTGGAATATTTTATTAA   350
   P   G   Q   Y   Q   F   S   G   E   Q   D   V   E   Y   F   I   K

GCTGGCCCATGAGCTGGGACTGCTGGTCATCCTGAGGCCGGGACCCTATA   400
 L   A   H   E   L   G   L   L   V   I   L   R   P   G   P   Y   I

FIG. 1A

```
TCTGTGCAGAGTGGGACATGGGACCATTACCTGCTTGGCTATTATTAAAA     450
  C*  A  E  W  D  M  G  G  L  P  A  W  L  L  L  K

GAATCTATTATTCTCCGTTCTTCTGATCCAGATTACCTTGCAGCTGTGGA     500
  E  S  I  I  L  R  S  S  D  P  D  Y  L  A  A  V  D

CAAATGGTGTGGAGTCCTCCTGCCCAAGATGAGGCCTCTCCTCTATCAGA     550
  K  W  L  G  V  L  L  P  K  M  K  P  L  L  Y  Q  N

ACGGAGGGCCGATTATAACCATGCAGGTTGAAAATGAATATGGCAGCTAC     600
  G  G  P  I  I  T  M  Q  V  E  N  E  Y  G  S  Y

TTTACCTGCGATTATGACTACCTGCGTTTCCTGCAGAAGCTCTTCCACCA     650
  F  T  C  D  Y  D  Y  L  R  F  L  Q  K  L  F  H

CCACCTGGGCAATGATGTACTTCTGTTCACCACTGATGGGGCAAATGAAA     700
  H  L  G  N  D  V  L  L  F  T  T  D  G  A  N  E  K

AGTTTCTGCAGTGCGGGGCTCTGCAGGCCTCTATGCCACAGTGGACTTT     750
  F  L  Q  C* G  A  L  Q  G  L  Y  A  T  V  D  F

GGACCAGGTGCCAACATCACTGCTGCTTTCCAAATCCAGAGAAAGAGTGA     800
  G  P  G  A  N  I  T  A  A  F  Q  I  Q  R  K  S  E
```

FIG. 1B

```
GCCCAAAGGACCATTGGTGAATTCTGAATTCTATACCGGCTGGTTGGATC      850
 P   K   G   P   L   V   N   S   E   F   Y   T   G   W   L   D   H

ATTGGGGCCAGCCACACTCAACAGTGAGGACTGAAGTGGTGGCTTCCTCC      900
  W   G   Q   P   H   S   T   V   R   T   E   V   V   A   S   S

CTCCATGATATACTTGCCCATGGGGCAAATGTGAACTTGTACATGTTCAT     1000
 L   H   D   I   L   A   H   G   A   N   V   N   L   Y   M   F   I

AGGTGGGACCAATTTTGCCTATTGGAATGGGGCCAACATGCCCTACCAAG     1050
  G   G   T   N   F   A   Y   W   N   G   A   N   M   P   Y   Q   A

CACAGCCCACCAGTTACGACTATGATGCCCCACTGAGCGAGGCAGGGGAC     1100
  Q   P   T   S   Y   D   Y   D   A   P   L   S   E   A   G   D

CTCACTGAGAAGTATTTTGCTCTGCGAGAAGTTATTCGGAAGTTTGAAAA     1150
 L   T   E   K   Y   F   A   L   R   E   V   I   R   K   F   E   K

AGTACCAGAAGGTTTTATCCCTCCGTCTACACCCAAGTTTGCATATGGAA     1200
  V   P   E   G   F   I   P   P   S   T   P   K   F   A   Y   G   K

AAGTTGCTCTGAAGAAGTTAAAGACGGTGGAGGAGGCCCTGAATGTTCTG     1250
  V   A   L   K   K   L   K   T   V   E   E   A   L   N   V   L
```

FIG. 1C

```
TGTCCGCCTGGGCCCATAAACAGCCTTTATCCCTTGACGTTTATCCAGGT   1300
 C*  P  P  G  P  I  N  S  L  Y  P  L  T  F  I  Q  V

GAAACAGTATTTCGGTTTTGTGATGTACCGAACAACACTTCCTCAAGACT   1300
  K  Q  Y  F  G  F  V  M  Y  R  T  T  L  P  Q  D  C

GCAGTGACCCCACACCCCTGTCTTCACCCCTCAGTGGAGTCCACGACCGC   1350
   S  D  P  T  P  L  S  S  P  L  S  G  V  H  D  R

GCCTATGTCTCTGTGGATGGGGTGCCCCAGGGAGTCATGGAGCGAAGTAA   1400
  A  Y  V  S  V  D  G  V  P  Q  G  V  M  E  R  S  N

TGTCATCACTCTGAACATAACCGGGAAGGCTGGAGCCACTCTGGACCTGC   1450
  V  I  T  L  N  I  T  G  K  A  G  A  T  L  D  L  L

TGGTGGAGAACATGGGACGTGTGAACTATGGCAGATATATCAATGATTTT   1500
   V  E  N  M  G  R  V  N  Y  G  R  Y  I  N  D  F

AAGGGCCTTATTTCTAACCTGACCCTTGGGTCCAGTATCCTCACAAACTG   1550
  K  G  L  I  S  N  L  T  L  G  S  S  I  L  T  N  W

GATGATCTTCCCGTTGAACACTGAGGATGCAGTACGCAGCCACCTGGGAG   1600
   M  I  F  P  L  N  T  E  D  A  V  R  S  H  L  G  G
```

FIG. 1D

```
GCTGGCATGGCCCTAACAATGGCCGCCATGATAAAACCTTTGCCCACCGC   1650
  W  H  G  P  N  N  G  R  H  D  K  T  F  A  H  R

TCGTCTAACTACACGCTCCCGGCCTTTTATATGGGGAACTTCTCTATTCC   1700
  S  S  N  Y  T  L  P  A  F  Y  M  G  N  F  S  I  P

CAGTGGGATCCCAGACTTGCCCCAGGACACCTTTATCCAGTTTCCTGGAT   1750
   S  G  I  P  D  L  P  Q  D  T  F  I  Q  F  P  G  W

GGACCAAGGGTCAGGTGTGGATTAATGGCTTTAACCTCGGTCGATATTGG   1800
   T  K  G  Q  V  W  I  N  G  F  N  L  G  R  Y  W

CCAGCACGGGGCCCCCAGATGACTTTGTTTGTGCCACGGCACATCCTGGT   1850
  P  A  R  G  P  Q  M  T  L  F  V  P  R  H  I  L  V

GACATCAACCCCAAACACCATCATGGTGCTGGAACTGGAGCACGCGCCCT   1900
  T  S  T  P  N  T  I  M  V  L  E  L  E  H  A  P  C*

GTGGTGACAGTGGCCCAGAAGTGTGCACCGTGGAGTTTGTGGACAGGCCG   1950
   G  D  S  G  P  E  V  C* T  V  E  F  V  D  R  P

GTTATCGGTGCCCCTCCAACCCCTGGTCATCCCCCTCCAGACCTGTCCCA   2000
  V  I  G  A  P  P  T  P  G  H  P  P  P  D  L  S  H
```

FIG. 1E

TCGAGACTTGAGACTGGACTATGTCTGAtgatgaaacactgtgacccgtt   2050

R   D   L   R   L   D   Y   V   *    (SEQ ID NO: 2)

ggagtttcagccttgcacgtacatcacctatcccctgtgtaatgccaac   2100 actcactggaaagttcaactggaaaatagatttagagtgtgcattttctc   2150 ctgaggtttccaggcagcctggtagtgcccaagcctccactggcaggggc   2200 caccatgaatgcatgatgagggcagtggcacacagtttggaatggaagct   2250 ttgaaggtgttcctgatttttatttggaggaatcatgttgtctttctgt   2300 taaataaaatttgtattcaaat    (SEQ ID NO: 1)   2322

FIG. 1F

CANINE β-GALACTOSIDASE GENE AND GM1-GANGLIOSIDOSIS

BACKGROUND OF THE INVENTION

1. Field of the Invention

The present invention relates generally to the fields of genetics, human genetics, and inherited metabolic disorders. More specifically, the present invention relates to an animal model for the study of $G_{M1}$-gangliosidosis.

2. Description of the Related Art $G_{M1}$-gangliosidosis, a lysosomal storage disorder which affects brain and multiple systemic organs, is due to an autosomal recessively inherited deficiency of acid β-galactosidase. This disease is clinically classified into three types based on, age at onset of clinical manifestations and on the degree of pathological changes. $G_{M1}$-gangliosidosis causes progressive neurologic and systemic impairments. Deficiency of acid β-galactosidase is also associated with Morquio B disease, which is primarily a skeletal-connective tissue disorder without primary central nervous system involvement (Suzuki et al., 1995; Alroy et al., 1985; Kaye et al., 1997; Nishimoto et al., 1991).

Acid β-galactosidase is a lysosomal hydrolase that cleaves β-linked terminal galactosyl residues from gangliosides, glycoproteins, and glycosaminoglycans, as well as from a variety of artificial substrates (Morreau et al., 1991). A full-length cDNA for human β-galactosidase has been cloned (Morreau et al., 1991; Oshma et al., 1988; Yamamoto et al., 1990), and point mutations and duplications in the human acid β-galactosidase gene have been identified in patients with $G_{M1}$-gangliosidosis (Suzuki et al., 1995; Kaye et al., 1997; Nishimoto et al., 1991; Oshima et al., 1992; Yoshida et al., 1992; Isii et al., 1995; Yoshida et al., 1991; Oshima et al., 1991).

There is no specific treatment for $G_{M1}$-gangliosidosis. The potential of gene therapy as a therapeutic approach for several lysosomal storage diseases is now under consideration (Ahern-Rindell et al., 1996). However, prior to human application, these potential treatments must be established to be efficacious and nontoxic in experimental animals.

Animal models of genetic diseases similar to ones known to exist in humans are valuable and essential research tools. These models permit investigations of pathogenesis and the evaluation of potential therapeutic approaches. Canine $G_{M1}$-gangliosidosis is an excellent model for the human disease. The canine disease resembles the human disease genetically, clinically, biochemically, and pathologically (Suzuki et al., 1995; Ahern-Rindell et al., 1996).

To study the molecular pathology of canine $G_{M1}$-gangliosidosis and possibilities for gene therapy, knowledge of the full-length cDNA sequence for canine β-galactosidase and its molecular defects in canine $G_{M1}$-gangliosidosis are essential. Canine $G_{M1}$-gangliosidosis has been described in several dog breeds, and the biochemical and enzymatic changes resulting from the disease have been studied (Alroy et al., 1985; Read et al., 1976; Rodriguez et al., 1982; Saunders et al., 1988; Alroy et al., 1992; Shell et al., 1989; Rittmann et al., 1980). However, the sequence of the full-length cDNA encoding canine β-galactosidase has not been previously published. Furthermore, the molecular defects responsible for $G_{M1}$-gangliosidosis in these canine models have not been characterized (Suzuki et al., 1995). Only a partially deduced normal canine β-galactosidase amino acid sequence lacking the 5' encoding region has been reported (Ahern-Rindell et al., 1996). However, the corresponding partial nucleotide sequence was not presented. Also, no nucleotide sequence data has been reported for the 5' encoding and untranslated regions as well as the 3' untranslated region. Although canine cDNA libraries were screened by the polymerase chain reaction, the 5' encoding region of the canine β-galactosidase gene was not detected (Ahern-Rindell et al., 1996).

$G_{M1}$-gangliosidosis occurs in the Portuguese Water (PW) dogs. For breeding purposes, it is important to set carrier dogs apart. Although the enzyme assay has facilitated carrier diagnosis, enzymatic detection of carriers is not always reliable because varying degrees of overlap in enzyme activity can occur between normal homozygotes and heterozygous carriers (Suzuki et al., 1995). To solve this problem, it was necessary to isolate a normal full-length cDNA encoding the canine acid β-galactosidase and search for the molecular defects which causes canine $G_{M1}$-gangliosidosis.

The prior art is deficient in the lack of a normal full-length cDNA encoding the canine acid β-galactosidase, methods of screening for the molecular defects which causes $G_{M1}$-gangliosidosis, and an animal model for the study of the molecular mechanisms of $G_{M1}$-gangliosidosis and other lysosomal storage disorders. The present invention fulfills these longstanding needs and desires in the art.

SUMMARY OF THE INVENTION

In the present study, normal Portuguese Water (PW) dogs and Portuguese Water dogs with $G_{M1}$-gangliosidosis were used. A full-length cDNA encoding canine acid β-galactosidase was isolated and sequenced, and a homozygous recessive mutation that causes canine $G_{M1}$-gangliosidosis was identified. This enables the classification of Portuguese Water dogs according to their genotypes with respect to this specific canine β-galactosidase gene mutation. A comparison was made between the DNA assay and the enzyme assay for β-galactosidase. These data are useful for the study of the molecular pathogenesis and potential gene therapy of $G_{M1}$-gangliosidosis.

In one embodiment of the current invention, an isolated DNA molecule encoding the full length cDNA sequence of canine β-galactosidase is provided. This DNA molecule has the sequence shown under SEQ ID No.: 1.

Another embodiment of the current invention comprises a plasmid containing SEQ ID No. 1 and regulatory elements necessary for expression of the canine acid β-galactosidase protein in a cell.

Another embodiment of the instant invention is the deduced amino acid sequence of β-galactosidase protein encoded by SEQ ID No.: 1. The deduced amino acid sequence of this protein is SEQ ID No.:2.

In another embodiment of the current invention, a R60H mutation of the canine acid β-galactosidase is described resulting from a substitution of $G^{200}$ with A. This causes an amino acid $Arg^{60}$ to His mutation in the protein and results in $G_{M1}$-gangliosidosis in a homozygous affected case.

Another embodiment of the instant invention comprises oligonucleotides with sequences corresponding to SEQ ID Nos. 21 and 22.

In yet another embodiment of the instant invention, a method which readily distinguishes affected homozygous recessive and heterozygous carriers of canine $G_{M1}$-Gangliosidosis from normal homozygotes is described. This method is capable of determining whether the dog has a R60H mutation in the heterozygous or homozygous state.

An appropriate fragment for analysis is generated by PCR amplification of exon 2 of the acid β-galactosidase gene, preferably utilizing set of primers #10 (SEQ ID Nos.: 21–22). PmlI digestion of exon 2 indicates the presence of the R60H mutation. Alternatively, the mutation can be detected by DNA sequence analysis of exon 2.

In a preferred embodiment, Portuguese Water dogs are genotypically analyzed to screen for the R60H mutation by isolating their genomic DNA from candidate dog samples (blood and/or tissues). PCR amplification of exon 2 of the acid β-galactosidase gene is performed with oligonucleotides, e.g., SEQ ID No. 21 and SEQ ID No. 22. The PCR products are then digested with PmlI restriction endonuclease, and the resulting fragments digested with PmlI are resolved by size using gel electrophoresis. A single fragment of 195 bp indicates that a dog has normal alleles for the acid β-galactosidase gene. Two fragments of 114 and 81 bp indicate that a dog has a homozygous R60H mutation of the acid β-galactosidase gene (i.e., both alleles of this gene are mutated), while the presence of three fragments of 195, 114, and 81 b.p. indicates that a dog has a heterozygous mutation (i.e., one allele of this gene is mutated, while the other one is normal).

The instant invention is also directed to a kit containing the materials necessary to perform this screen for the R60H mutation of the canine acid β-galactosidase. This kit would consist of reagents for the isolation of genomic DNA from samples, oligonucleotides SEQ ID Nos.: 21 and 22, reagents for PCR amplification, and the PmlI restriction endonuclease.

In yet another embodiment of the instant invention, Portuguese Water dogs can be screened to determine which dogs are carriers of $G_{M1}$-gangliosidosis. If PCR amplification and PmlI digestion of exon 2 of the acid β-galactosidase gene yields fragments of 145, 114, and 81 bp, the dog in question has the R60H heterozygous mutation and is a carrier of $G_{M1}$-gangliosidosis. The dog can then be excluded from any breeding programs.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIGS. 1A–1F show the nucleotide (SEQ ID No. 1) and deduced amino acid sequences (SEQ ID No. 2) of Portuguese Water dog β-galactosidase. Lower-case letters indicate the 5' and 3' untranslated sequences. The methionine encoded by the first ATG is designated amino acid 1. The putative signal sequence cleavage site is indicated by an arrow. The potential glycosylation sites are underlined. The cysteine residues are in bold-lettering and marked with asterisks. The AATAAA (SEQ ID No. 3) sequence in the 3'-untranslated region is in bold-lettering and underlined.

DETAILED DESCRIPTION OF THE INVENTION

Figure 2:
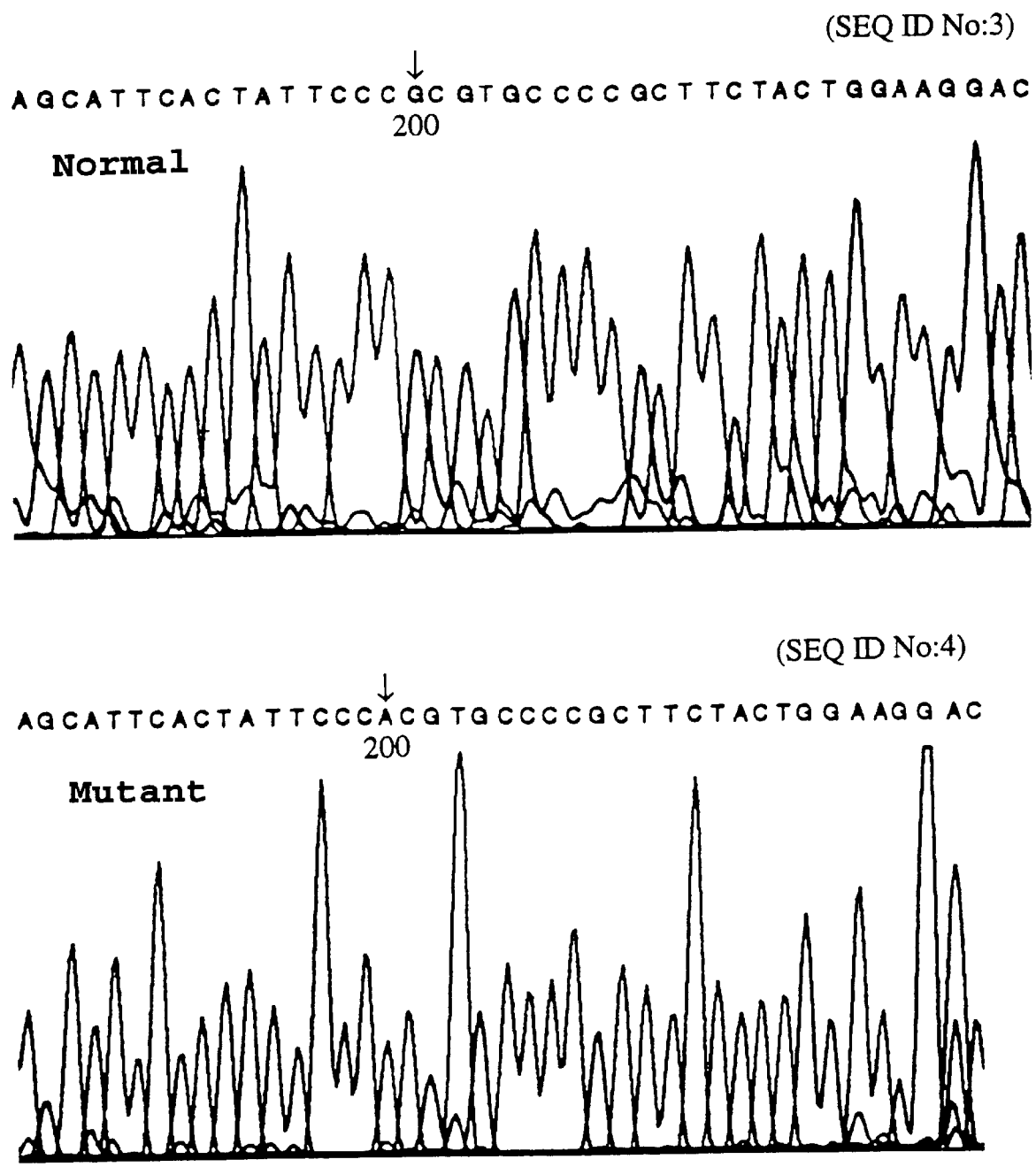
FIG. 2 shows the normal (SEQ ID No. 4) and R60H mutant (SEQ ID No. 5) sequences of cDNA for the Portuguese Water dog acid β-galactosidase by automated sequencing. The sequences (reading 5' to 3' from left) shows a nucleotide change from $G^{200}$ in normal dog to $A^{200}$ in a Portuguese Water dog with $G_{M1}$-gangliosidosis, which is marked with an arrow.

In accordance with the present invention there may be employed conventional molecular biology, microbiology, recombinant DNA techniques, and enzymology within the skill of the art. Such techniques are explained fully in the literature. See, e.g., Maniatis, Fritsch & Sambrook, "Molecular Cloning: A Laboratory Manual (2nd. ed. 1989); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

As used herein, the term "cDNA" (complementary DNA) shall refer to DNA synthesized from a mRNA template using reverse transcriptase.

As used herein, the term "derived amino acid sequence" shall mean the amino acid sequence determined by reading the triplet sequence of nucleotide bases in the cDNA.

As used herein the term "screening a library" shall refer to the process of using a labeled probe to check whether, under the appropriate conditions, there is a sequence complementary to the probe present in a particular DNA library. In addition, "screening a library" could be performed by PCR.

As used herein, the term "PCR" refers to the polymerase chain reaction that is the subject of U.S. Pat. Nos. 4,683,195 and 4,683,202 to Mullis, as well as other improvements now known in the art.

The amino acid described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J Biol. Chem.*, 243:3552–59 (1969), abbreviations for amino acid residues are known in the art.

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be inserted so as to bring about the replication of the inserted segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included in the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide", as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as a purified restriction digested fragment or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer must be sufficiently long to prime the synthesis of the desired extension product in the presence of the inducing agent. The exact length of the primer will depend upon many factors, including temperature, source of primer, and the use of a method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementary with the sequence or hybridize therewith and thereby form the template for the synthesis of the extension product.

As used herein, the terms "restriction endonucleases" and "restriction enzymes" refer to enzymes, each of which cut double-stranded DNA at or near a specific nucleotide sequence.

A cell has been "transformed" by exogenous or heterologous DNA when such DNA has been introduced into the cell. The transforming DNA may or may not be integrated (covalently linked) into the genome of the cell. In prokaryotes, yeast, and mammalian cells for example, the transforming DNA may be maintained on an episomal element such as a plasmid. A "clone" is a population of cells derived from a single cell or ancestor by mitosis. "cell line" is a clone of a primary cell that is capable of stable growth in vitro for many generations.

Two DNA sequences are "substantially homologous" when at least about 75% (preferably at least about 80%, and most preferably at least about 90% or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous' region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, coding sequence is a construct where the coding sequence itself is not found in nature (e.g., a cDNA sequence of a gene of eukaryotic cells is not completely identical with its genomic sequence. The former does not contain introns, while the latter includes introns). Allelic variations or naturally-occurring mutational events do not give rise to a heterologous region of DNA as defined herein.

The labels most commonly employed for these studies are radioactive elements, enzymes, chemicals which fluoresce when exposed to ultraviolet light, and others.

Rapid amplification of cDNA ends (RACE) is a procedure for amplification of nucleic acid sequences from a messenger RNA (mRNA) template between a defined internal site and unknown sequences at either the 3' or 5' end of the mRNA. 5' RACE is a technique that facilitates the isolation and characterization of 5' ends from low-copy number messages. First strand cDNA synthesis is primed using a gene-specific antisense oligonucleotide (GSP1). This permits cDNA conversion of specific mRNA or related families of mRNAs, and maximizes the potential for complete extension to the 5'-end of the message. Tailed cDNA is then amplified by PCR using a mixture of three primers: a nested gene-specific primer (GSP2), which anneals 3' to GSP1; and a combination of a complementary homopolymer-containing anchor primer and corresponding adapter primer which permits amplification from the homopolymeric tail. This allows amplification of unknown sequences between the GSP2 and the 5'-end of the mRNA.

In vitro site-directed mutagenesis is an invaluable technique for studying protein structure-function relationships, gene expression, and vector modification. The double strand, site-directed mutagenesis kit allows site-specific mutation in virtually any double-strand plasmid, thus eliminating the need for subcloning into M13-based bacteriophage vectors and for single-strand DNA rescue.

The assay procedure for β-galactosidase activity is based on the principle that the enzyme cleaves 4-methyl umbelliferyl β-galactoside (4-MU β-gal) to yield 4-methyl umbelliferone (4-MU) and galactose. The liberated 4-MU is highly fluorescent in alkaline pH with excitation at 350 nm and emission at 440 nm. Based on the intensity of fluorescence, the amount of 4-MU in nmoles is calculated from a standard curve of known concentrations (nmoles of 4-MU0. Similarly, β-hexosaminidase activity is determined using 4-MU-β-D-N-acetyl glucosaminide (4-MU-β-hex) as substrate. Fluorescence of the sample is read in a spectrophotometer with excitation at 350 nm and emission at 440 nm.

Theoretically, carriers would have 50% of normal activity of lysosomal β-galactosidase. Because normal activity for this enzyme may vary over a wide range in individual dogs, it is possible to find carrier values overlapping with borderline levels of normal values. Since lysosomal β-hexosaminidase activity is unaffected in this disease, the principle of expression of β-galactosidase activity as a ration of β-hexosaminidase activity was utilized. This ration provides better discrimination of carriers from control normal dogs. However, identification of carriers is not absolute.

As used herein, the term "host" is meant to include not only prokaryotes but also eukaryotes such as yeast, plant and animal cells. A recombinant DNA molecule or gene of the present invention which encodes a protein can be used to transform a host using any of the techniques commonly known to those of ordinary skill in the art. Especially preferred is the use of a vector containing coding sequences for the DNA molecule or a gene of the present invention which encodes a protein of the present invention for purposes of prokaryote transformation and transfection of eukaryotic cells. Prokaryotic hosts include *E. coli, S. tymphimurium, Serratia marcescens* and *Bacillus subtilis*. Eukaryotic hosts include yeasts, mammalian cells, and insect cells.

In general, the expression vector typically contains an origin of replication, promoter(s), terminator(s), as well as specific genes which are capable of providing phenotypic selection in transformed cells. The transformed hosts can be cultured according to means known in the art to achieve optimal cell growth.

Methods which are well known to those skilled in the art can be used to construct expression vectors containing appropriate transcriptional and translational control signals. See for example, the techniques described in Sambrook et al., 1989, *Molecular Cloning: A Laboratory Manual* (2nd Ed.), Cold Spring Harbor Press, N.Y. A gene and its transcription control sequences are defined as being "operably linked" if the transcription control sequences effectively control the transcription of the gene. Vectors of the invention include, but are not limited to, plasmid vectors and viral vectors.

In the present study, a full-length cDNA encoding the canine β-galactosidase was isolated and sequenced. Normal Portuguese Water dogs and Portuguese Water dogs with $G_{M1}$-gangliosidosis were used to identify a homozygous recessive mutation that causes canine $G_{M1}$-gangliosidosis. This allows Portuguese Water dogs to be classified according to their genotypes with respect to this specific canine β-galactosidase gene mutation. Furthermore, a correlation was observed between the DNA assay and the enzyme assay for β-galactosidase. The canine model is useful for the study of the molecular pathogenesis and potential gene therapy of $G_{M1}$-gangliosidosis.

The current invention is directed to SEQ ID No.: 1, comprising an isolated DNA molecule encoding the full length cDNA sequence of canine acid β-galactosidase The current invention is also directed to a plasmid containing the full length canine acid β-galactosidase cDNA and regulatory elements necessary for expression of the encoded protein in cells.

The instant invention is also directed to a β-galactosidase protein encoded by SEQ ID No.: 1 with an amino acid sequence of SEQ ID No.: 2.

A homozygous R60H mutant allele of the acid β-galactosidase gene is described in which of $G^{200}$ is mutated to A. This causes an amino acid $Arg_{60}$ to His mutation in the protein and results in $G_{M1}$-gangliosidosis in the homozygous affected dog.

The instant invention also provides oligonucleotides for amplification of exon 2 of the canine acid β-galactosidase gene. The sequences of these oligonucleotides are given in SEQ ID Nos. 21 and 22.

The instant invention is also directed to methods of identifying Portuguese Water dogs which are carriers and homozygous affected cases of canine $G_{M1}$-Gangliosidosis as well as homozygous normal. This is accomplished by determining whether the dog carries a R60H mutation. An appropriate fragment for analysis is generated by PCR amplification of exon 2 of the acid β-galactosidase gene. The oligonucleotides described by SEQ ID Nos.: 21–22 are particularly designed for this purpose. PmlI digestion of the PCR product of exon 2 can distinguish the genotype of the R60H mutation. Alternatively, the mutation can be detected by DNA sequence analysis.

A specific method for genetically screening the R60H mutation in Portuguese Water dogs is provided. Genomic DNA is isolated from dog blood samples. PCR amplification of exon 2 of the acid β-galactosidase gene is performed with oligonucleotides SEQ ID No. 21 and SEQ ID No. 22. The PCR amplification products are then digested with PmlI restriction endonuclease, and the resulting fragments are resolved by size using a method such as gel electrophoresis. Generation of a single fragment of 195 bp indicates that a dog has normal alleles for the acid β-galactosidase gene Two fragments of 114 and 81 bp indicate that a dog is homozygous for the R60H mutation of the acid β-galactosidase gene which causes $G_{M1}$-cgangliosidosis. Three fragments of 195, 114, and 81 bp indicate that a dog is a carrier of $G_{M1}$-gangliosidosis.

The instant invention is also directed to a kit containing the materials necessary to perform the screen for the R60H mutation of acid β-galactosidase. This kit would consist of reagents for the isolation of genomic DNA from samples, oligonucleotides SEQ ID Nos.: 21 and 22, reagents for PCR amplification, and the PmlI restriction endonuclease.

The instant invention is also directed to screening Portuguese Water dogs to eliminate carriers of $G_{M1}$-gangliosidosis from breeding programs. If PCR amplification and PmlI digestion of exon 2 of acid β-galactosidase yields three fragments of 195, 114, and 81 bp, the dog in question is a carrier of $G_{M1}$-gangliosidosis.

The following examples are given for the purpose of illustrating various embodiments of the invention and are not meant to limit the present invention in any fashion.

EXAMPLE 1

Blood and Tissue Samples.

Portuguese Water dog blood samples of 38 normal and 17 carriers, as well as brain and liver tissues of 4 affected Portuguese Water dogs of $G_{M1}$-gangliosidosis were provided by the Portuguese Water dog Club of America (Providence, R.I.). The dogs affected with $G_{M1}$-gangliosidosis were diagnosed by their clinical and pathological signs and by enzymatic assay. Normal dogs and carriers were identified by enzymatic assay of β-galactosidase. Additional genomic DNA samples from normal and carrier blood of 55 Portuguese Water dogs, whose status were not disclosed to the laboratory performing the molecular analysis until the genotype patterns were obtained, were provided by Dr. Gordon Lark (Utah University). The 55 samples were analyzed in a blind study to confirm the use of the DNA mutation assay.

EXAMPLE 2

Cell Culture

Portuguese Water dog β-galactosidase deficient fibroblasts GM 11474 (Coriell Institute for Medical Research, Camden, N.J.) were cultured at 37° C. in 5% $CO_2$ in Dulbecco's modified Eagle medium with 15% fetal bovine serum, 2× concentration of amino acids and vitamins (DMEM, GIBCO, Gaithersburg, Md.).

EXAMPLE 3

Extraction of Total RNA, mRNA, and Genomic DNA from Blood and Tissues

Portuguese Water dog lymphocytes from blood were prepared by a standard method. Total RNA, mRNA, genomic DNA from lymphocytes, fibroblasts, or tissue samples were extracted, using the appropriate protocols for isolation of total RNA (RNAgents Total RNA Isolation System, Promega, Madison, Wis.), mRNA (Fast Track mRNA Isolation Kit, InVitrogen, Carlsbad, Calif.), and genomic DNA (Puregene, Gentra Systems, Minneapolis, Minn.), as suggested by the respective manufacturers.

EXAMPLE 4

Methods for the Synthesis and Amplification of cDNA

First strand cDNA synthesis and amplification of cDNA between nucleotides 118 and 1920 were performed using the GeneAmpRNA PCR kit under the conditions recommended by the manufacturer (Perkin Elmer, Foster, Calif.). The designation of nucleotide numbers is shown in FIGS. 1A–1F. Four sets of primers (#1–4) (SEQ ID Nos. 6–13), shown in table 1, were designed from a partial, previously isolated cDNA sequence of β-galactosidase from mongrel dog, which lacked the 5' and 3' encoding regions of the gene. Four overlapping PW dog β-galactosidase cDNA fragments (nucleotides 118–444, 368–802, 752–1185, 1112–1920 of SEQ ID No. 1) were amplified by polymerase chain reaction (PCR).

TABLE 1

Primers used in isolating and sequencing the full-length cDNA of the PW dog acid β-galactosidase and its mutation

| Primer Set | | Sequence | SEQ ID No. |
|---|---|---|---|
| 1 | Forward | 5'-TTC-ACA-ATT-GAC-TAC-AGC-CAC-3' | (SEQ ID No: 6) |
|  | Reverse | 5'-TAA-TAG-CCA-AGC-AGG-TAA-TC-3' | (SEQ ID No: 7) |
| 2 | Forward | 5'-GAC-TGC-TGG-TCA-TCC-TG-3' | (SEQ ID No: 8) |
|  | Reverse | 5'-GCT-CAC-TCT-TTC-TCT-GGA-TTT-G-3' | (SEQ ID No: 9) |
| 3 | Forward | 5'-GAC-CAG-GTG-CCA-ACA-TCA-CT-3' | (SEQ ID No: 10) |
|  | Reverse | 5'-CTC-CTC-CAC-CGT-CTT-TAA-CT-3' | (SEQ ID No: 11) |

TABLE 1-continued

Primers used in isolating and sequencing the full-length
cDNA of the PW dog acid β-galactosidase and its mutation

| Primer Set | | Sequence | SEQ ID No. |
|---|---|---|---|
| 4 | Forward | 5'-GTT-TTA-TCC-CTC-CGT-CTA-CAC-C-3' | (SEQ ID No: 12) |
|   | Reverse | 5'-TTC-TGG-GCC-ACT-GTC-ACC-3' | (SEQ ID No: 13) |
| 5 | Reverse | 5'-GGC-CAC-GCG-TCG-ACT-AGT--ACT-TTT-TTT-TTT-TTT-TTT-T-3' | (SEQ ID No: 14) |
| 6 | Reverse | 5'-CAT-GTC-CCA-CTC-TGC-ACA-GAT-3' | (SEQ ID No: 15) |
| 7 | Forward | 5'-TGA-TCT-TCC-CGT-TGA-ACA-CT-3' | (SEQ ID No: 16) |
| 8 | Forward | 5'-AGG-GAC-GTG-GCG-ACG-GCG-ATG-3' | (SEQ ID No: 17) |
|   | Reverse | 5'-CCG-CAG-GCC-GCG-CGC-AG-3' | (SEQ ID No: 18) |
| 9 | Forward | 5'-CAG-GTG-TGG-ATT-AAT-GGC-TT-3' | (SEQ ID No: 19) |
|   | Reverse | 5'-ACT-CCA-ACG-GGT-CAC-AGT-GTT-TC-3' | (SEQ ID No: 20) |
| 10 | Forward | 5'-CTT-GCT-CTG-CAG-AAT-GCT-TCC-3' | (SEQ ID No: 21) |
|   | Reverse | 5'-CCC-TCT-TAC-TTA-CGT-CTG-GAT-G-3' | (SEQ ID No: 22) |
| 11 | Forward | 5'-ATT-CAC-TAT-TCC-CAC-GTG-CCC-CGC-TTC-3' | (SEQ ID No: 23) |
| 12 | Forward | 5'-CTG-TGA-CTG-GTG-ACG--CGT-CAA-CCA-AGT-C-3' | (SEQ ID No: 24) |

The 5' region of β-galactosidase cDNA was isolated from total dog RNA using the 5' race system kit for rapid amplification of G:C rich cDNA ends (GIBCO). Primers #5 (SEQ ID No. 14) and 6 (SEQ ID No. 15), as well as the reverse primer of set #1 (SEQ ID No. 7), described in table 1 were utilized for isolation of the 5' region of β-galactosidase cDNA. For isolation of the 3' region of β-galactosidase cDNA from total Portuguese Water dog RNA, the 3' race system kit for rapid amplification of cDNA ends (GIBCO) and the two primers, #5 (SEQ ID No. 14) and #7 (SEQ ID No. 16), shown in table 1, were used. The procedures and conditions recommended by the manufacturer (GIBCO) were followed. An entire cDNA coding region of β-galactosidase was isolated from total dog RNA using the forward primer of set #8 (SEQ ID No. 17) and the reverse primer of set #9 (SEQ ID No. 20), as well as Advantage 2 PCR kit (CLONTECH, Palo Alto, Calif.).

EXAMPLE 5
PCR Amplification of Genomic DNA

Based on the results of the cDNA sequencing, two sets of primers (#8–9) (SEQ ID Nos. 17–20), shown in table 1, were used to amplify genomic DNAs from the 5' and 3' regions of the β-galactosidase gene for confirmation of the cDNA sequence obtained from the 5' or 3' race systems. Also, a sets of primers (#10) (SEQ ID Nos. 21-22), shown in table 1, was synthesized according to sequences overlapping the exon-intron boundaries (Ahern-Rindell et al., 1996) and the cDNA sequence of exon 2 described herein. These primers were used for amplification of the corresponding genomic DNA fragment of this exon.

EXAMPLE 6
Sequence Analysis of cDNA and DNA

DNA and cDNA fragments amplified by PCR were inserted into the pCR-TOPO vector according to protocols suggested by the manufacturer (TOPO TA Cloning kit, InVitrogen). The clones containing the expected size fragments of cDNA and DNA were analyzed by automated sequencing. The primers, including T7, M13 reverse primers, the reverse primer of primer set #1 (SEQ ID No. 7), the #2 primer set (SEQ ID Nos. 8–9), the forward primer of primer sets #3 (SEQ ID No. 10) and 4 (SEQ ID No. 12), and primer #7 (SEQ ID No. 16) in table 1, were used to sequence the cDNA and the DNA.

EXAMPLE 7
Methods of in Vitro Mutagenesis and Expression

A cDNA including the entire encoding region of normal β-galactosidase was inserted into HindIII/XbaI-cut pcDNA3 (a stable expression vector in mammalian cells, InVitrogen). The site-specific mutation of β-galactosidase cDNA was performed under conditions recommended by the manufacturer (Chameleon double-stranded, site-directed mutagenesis kit, Stratagene, La Jolla, Calif.). The selection and mutagenic primers #11 (SEQ ID No. 23) and 12 (SEQ ID No. 24) are shown in Table 1. The β-galactosidase cDNA was sequenced completely to ensure that only the expected mutation was present. Portuguese Water dog β-galactosidase-deficient fibroblasts were respectively transfected with 5 µg of vector containing either a normal or a mutant β-galactosidase cDNA in conjunction with 20 µg of DOTAP liposome (Boehringer-Mannheim, Indianapolis, Ind.) in each 60-mm dish. The cells were harvested after 60 hours and the β-galactosidase activity was assayed.

EXAMPLE 8
β-galactosidase and β-hexosaminidase Enzyme Assay

Activity of lysosomal acid β-galactosidase and β-hexosaminidase in homogenized cells was determined according to the method of Kolodny et al. (1976) and Hotamisligil et al. (1993). Statistical analysis of the data utilized standard statistical methods, including student's t test, analysis of variance, and false positive value.

EXAMPLE 9
Sequencing of the Canine β-Galactosidase Gene

Using four sets of primers (#1–4) (SEQ ID Nos. 6–13), four overlapping Portuguese Water dog β-galactosidase cDNA fragments were generated and sequenced. The sequences of these cDNA fragments were the same as the corresponding regions of mongrel dog cDNA. Based on the partial normal sequence obtained from Portuguese Water dog β-galactosidase cDNA, cDNA for the 5' and 3' regions of the Portuguese Water dog β-galactosidase were extended and isolated. A cDNA fragment of more than 500 bp from the 5' region and a cDNA fragment of approximately 800 bp from the 3' region were isolated and sequenced. To further confirm the cDNA sequences of the 5' and 3' regions, the 5' and 3' encoding regions of genomic DNA for the Portuguese Water dog β-galactosidase were also isolated and sequenced. The sequences obtained from the genomic DNA were identical with the cDNA sequence.

EXAMPLE 10
Characterization of the Canine β-Galactosidase Gene

As shown in FIGS. 1A–1F, the 2322-nucleotide cDNA sequence (SEQ ID No. 1) of Portuguese Water dog acid β-galactosidase consists of a 2004-nucleotide sequence encoding a protein of 668 amino acids, a 21-nucleotide 5'-untranslated region, and a 297-nucleotide 3'-untranslated region. The 3'-untranslated region contains the AATAAA (SEQ ID No.: 3) sequence characteristic of a 3'-cleavage signal. The GC content of the first 240-nucleotide sequence is approximately 66%. The deduced amino acid sequence (SEQ ID No. 2) contains a 24-amino acid putative signal sequence that satisfies the criteria for a signal sequence (Watson, 1984; Von Heijne, 1983). The GC content of the putative signal sequence represents approximately 74% of the total nucleotides. The signal sequence of Portuguese Water dog acid β-galactosidase has one more amino acid than that predicted on the basis of the human signal sequence (Ahern-Rindell et al., 1996). The deduced amino acid sequence includes 6 possible glycosylation sites (Asn-X-Thr or -Ser), located at positions 27, 248, 465, 499, 546, 556, as well as 7 cysteine residues.

EXAMPLE 11
Comparison of the Portuguese Water dog β-galactosidase Gene to the Partially Deduced Canine Amino Acid Sequence The deduced amino acid sequence of the Portuguese Water dog β-galactosidase is consistent with the corresponding region of a partial deduced canine amino acid sequence (Ahern-Rindell et al., 1996), except for three amino acid changes. The three discrepancies are amino acids $Arg^{60}$ $Lys^{227}$, and $Gly^{342}$ in the sequence (SEQ ID No. 2) of FIGS. 1A–1F, numbered respective $His^{59}$, Leu 226, and $Ala^{341}$ in the published partial sequence (Ahern-Rindell et al., 1996). When the deduced amino acid sequence of the Portuguese Water dog β-galactosidase was analyzed by hydrophobicity, a large hydrophilic region was shown in the area of amino acids 528–547.

EXAMPLE 12
Gene Mutation Analysis

After obtaining a normal full length canine cDNA sequence, the full length cDNA from the Portuguese Water dog β-galactosidase deficient fibroblasts was isolated and sequenced. A missense (G to A transition) mutation was identified at nucleotide position 200 in exon 2, which induces an amino acid change from $Arg^{60}$ to His (mutation R60H, FIG. 2). This mutation was confirmed by analysis of genomic DNA of exon 2 from Portuguese Water dogs of normal, carrier, and affected cases with $G_{M1}$-gangliosidosis. Genomic sequence information of exon 2 was found to be identical to the corresponding area of the cDNA sequence.

EXAMPLE 13
Genotype Analysis of R60H Mutation.

Figure 3:
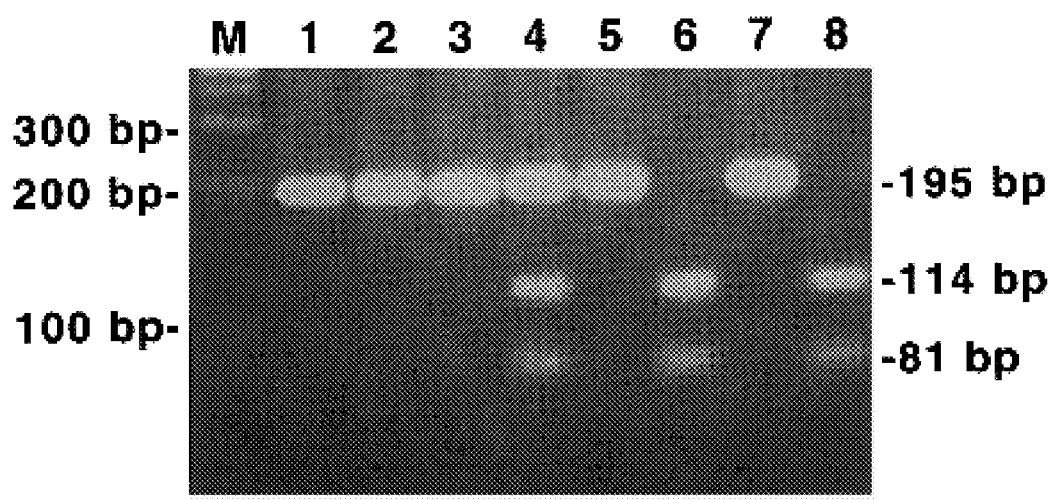
FIG. 3 shows genotype determination of Portuguese Water dogs affected with $G_{M1}$-gangliosidosis, carriers, and normal Portuguese Water dogs by PCR and restriction analysis (PmlI). M: marker; 1: normal Portuguese Water dog DNA without digestion; 2: normal Portuguese Water dog DNA digested with PmlI (homozygous normal); 3: carrier DNA without digestion; 4: carrier DNA digested with PmlI (heterozygous); 5: DNA of fibroblasts from affected Portuguese Water dog (affected case 1) without digestion; 6: DNA of fibroblasts from affected case 1 digested with PmlI (homozygous mutation); 7: DNA of brain tissue from affected Portuguese Water dog (affected case 2) without digestion; 8: DNA of brain tissue from affected case 2 digested with PmlI.

The mutation ($CG^{200}C \rightarrow CAC$) created a new restriction enzyme site for PmlI (CACGTG) (SEQ ID No. 25). This permits genotype analysis based on different band fragments observed following PCR amplification of genomic DNA with primer set #10 (SEQ ID Nos.: 21–22) and restriction enzyme digestion of the resulting PCR fragment. The data, shown in FIG. 3, confirmed that this mutation is recessively homozygous in affected dogs with $G_{M1}$-gangliosidosis. After digestion with PmlI, a 195 bp DNA fragment of affected Portuguese Water dogs with $G_{M1}$-gangliosidosis produces two fragments of 114 and 81 bp bands, respectively. Carriers produce three fragments of 195, 114, and 81 bp bands, whereas the normal DNA fragment of exon 2 is not digested by PmlI so that only one 195 bp band appears. Using this DNA mutation analysis, 115 genomic DNA samples were examined, revealing 60 normal homozygotes, 50 heterozygous carriers, and 5 affected cases for this homozygous recessive mutation. The data were compatible with those of the enzyme assay except for a few discrepancies described below.

EXAMPLE 14
Mutant Gene Expression.

Figure 4:
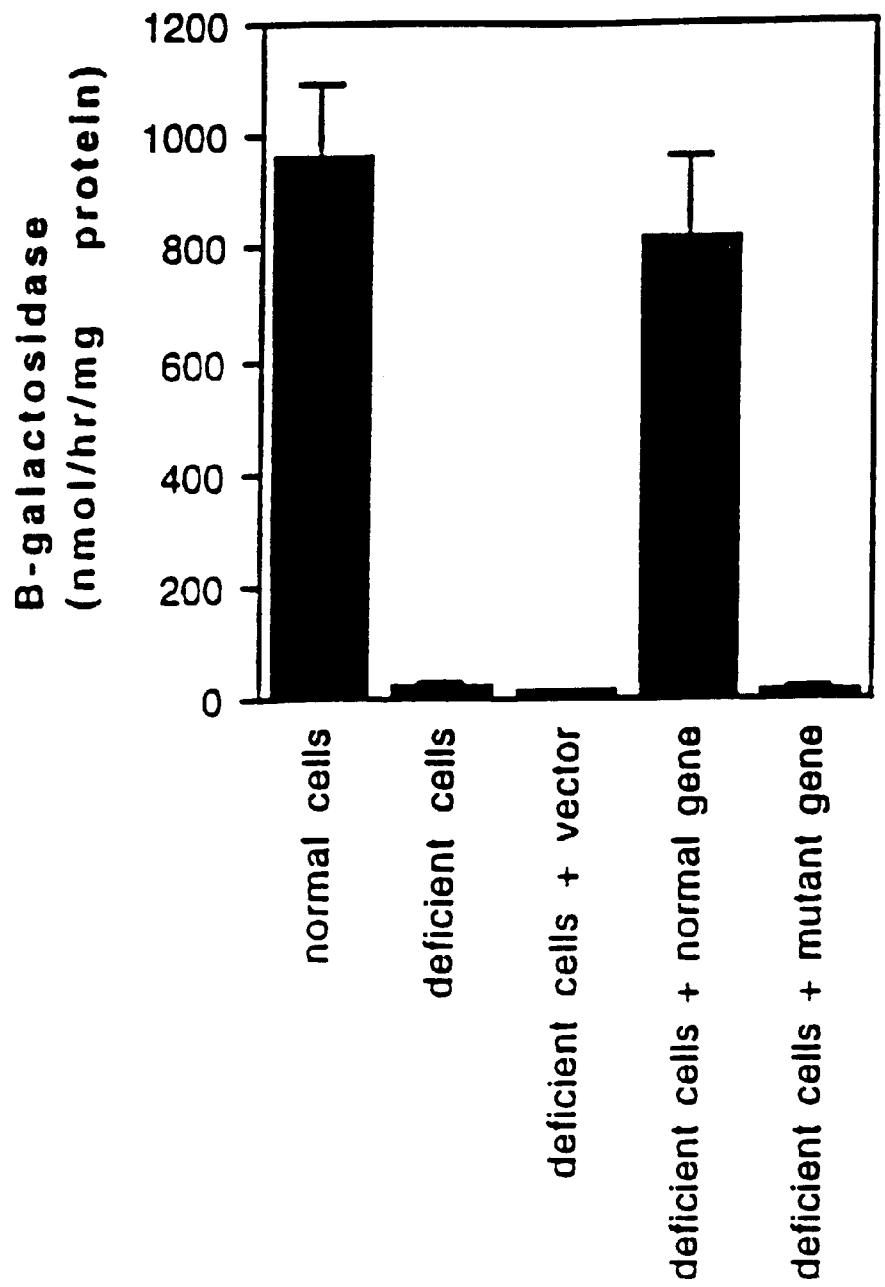
FIG. 4 shows β-galactosidase activity of deficient Portuguese Water fibroblast cells before and after transfection with a vector containing either normal or mutant canine β-galactosidase cDNA. Normal cells: normal dog fibroblasts; deficient cells: deficient fibroblasts from affected Portuguese Water dog; deficient cells+vector: deficient fibroblasts transfected with the vector alone; deficient cells+ normal gene: deficient fibroblasts transfected with the vector containing the full length normal β-galactosidase cDNA; and deficient cells+mutant gene: deficient fibroblasts transfected with the vector containing the full length mutant β-galactosidase cDNA.

To confirm that β-galactosidase deficiency is induced by this mutation, the in vitro expression of normal and mutant full length cDNA of Portuguese Water dog acid β-galactosidase was studied in Portuguese Water dog deficient fibroblasts. As shown in FIG. 4, the β-galactosidase activity was 26.3±5.7 nmol/hr/mg protein in Portuguese Water dog deficient fibroblasts. Following exon 2 from the affected Portuguese Water dogs with $G_{M1}$-gangliosidosis produces two fragments of 114 and 81 bp bands, respectively. Carriers produce three fragments of 195, 114, and 81 bp bands, whereas the normal DNA fragment of exon 2 is not digested by PmlI so that only one 195 bp band appears. Using this DNA mutation analysis, 115 genomic DNA samples were examined, revealing 60 normal homozygotes, 50 heterozygous carriers, and 5 affected cases for this homozygous recessive mutation. The data were compatible with those of the enzyme assay except for a few discrepancies described below.

EXAMPLE 14
Mutant Gene Expression.

To confirm that β-galactosidase deficiency is induced by this mutation, the in vitro expression of normal and mutant full length cDNA of Portuguese Water dog acid β-galactosidase was studied in Portuguese Water dog deficient fibroblasts. As shown in FIG. 4, the β-galactosidase activity was 26.3±5.7 nmol/hr/mg protein in Portuguese Water dog deficient fibroblasts. Following introduction of normal β-galactosidase cDNA into the deficient fibroblasts, the enzyme activity increased markedly (821.2±140.1 nmol/hr/mg protein) as compared with that of the parental deficient fibroblasts and deficient fibroblasts transfected with vector alone. The activity reached approximately 86% of the normal level of β-galactosidase activity (959.5±133.3). In contrast, the β-galactosidase activity remained unchanged in the cells transfected with the mutant cDNA.

EXAMPLE 15
Comparison of the DNA Mutation Assay and Enzymatic Assay

To distinguish possible overlap in enzyme activity occurring between normal homozygotes and heterozygous carriers, the data of the DNA mutation assay was compared with the enzyme assay in 55 cases. Reference ranges for enzymatic activities in carrier and normal Portuguese Water dogs were previously established, i.e, the ratio of β-hexosaminidase to β-galactosidase (β-Hex/β-Gal) was ≧20±3 for carrier, whereas ≦10±3 was normal. Based on the results of the enzyme assay, 19 cases were determined as normal, and 36 cases were previously regarded as carriers (Table 2). Of these 36 carriers, the enzymatic ratios of 8 cases were in the border-line level or inconclusive range between normal and carrier. The DNA mutation assay revealed that 5 of the 8 cases were confirmed as carriers, whereas 3 of the 8 cases were normal b y genotyping. Thus, the DNA mutation assay identified 33 heterozygous carriers and 22 normal homozygotes in 55 cases. Compared with the results of the DNA mutation assay, the false positive value for the enzyme assay was 13.6%. This indicates that the DNA mutation assay is more specific than the enzyme analysis of β-galactosidase for the determination of carriers.

TABLE 2

Comparison of the DNA mutation assay and enzyme assay for β-galactosidase

| | β-hexosaminidase/ β-galactosidase ratio | | DNA mutation analysis | |
|---|---|---|---|---|
| | n | mean ± SEM | n | genotype |
| Normal homozygotes | 19 | 6.5 ± 3.3 | 22 | normal |
| Carriers | 36 | 22.2 ± 8.3 | 33 | heterozygous |

EXAMPLE 16

Analysis of the Sequence of PW Dog Acid β-galactosidase

The present study shows the results of isolation and characterization of the full length cDNA sequence of Portuguese Water dog acid β-galactosidase. The nucleotide sequence identified herein and its deduced amino acid sequence are identical to the corresponding partial canine sequences found in GeneBank (Accession #AF056084), which lack the 5' encoding region, and are consistent with a partial deduced canine amino acid sequence (Ahern-Rindell et al., 1996) except for a few discrepancies described in the results herein. The reason for the few differences detected between the prior data and the data herein may be that they were derived from the use of different canine breeds. The cDNA sequences of acid β-galactosidase in different species of mice have also shown five discrepancies of nucleotides (Nanba and Suzuki, 1991).

A comparison between the human (Oshma et al., 1988; Yamamoto et al., 1990) and Portuguese Water dog cDNA encoding sequences indicates approximately 86.5% identity at the nucleotide level and about 81% identity at the amino acid level. The present data indicate that the total amino acids of dog acid β-galactosidase are 668, and not 667 as estimated previously (Ahern-Rindell et al., 1996). Therefore, the number of amino acids of dog acid β-galactosidase is 9 fewer than that of the human (677 amino acids) (Oshma et al., 1988; Yamamoto et al., 1990), and 21 more than that of the mouse (647 amino acids) (Nanba and Suzuki, 1990 and 1991).

The present results show that a signal sequence of Portuguese Water dog acid β-galactosidase contains 24 amino acids, which is one more amino acid than that of the human (Oshma et al., 1988; Yamamoto et al., 1990), but is the same as that of the mouse (Nanba and Suzuki, 1990 and 1991). There is less than 40% of homology between the dog and the human signal sequences. This explains the reason for unsuccessful amplification of the 5' encoding region using a 5' primer synthesized on the basis of the human 5' β-galactosidase sequence (Ahern-Rindell et al., 1996). Ahern-Rindell et al. reported only a partial, deduced normal canine β-galactosidase amino acid sequence lacking the 5' encoding region. However, the corresponding partial nucleotide sequence was not presented. Also, there is no published data of 5' encoding and untranslated regions, as well as of the 3' untranslated region. By using the 5' RACE system to isolate this region, the present study was able to circumvent the difficulty presented by the high GC content of this region and the earlier failure to isolate the 5' encoding region by screening canine cDNA libraries (Ahern-Rindell et al., 1996). The glycosylation sites and cysteine residues in the PW dog β-galactosidase are the same as those previously reported (Ahern-Rindell et al., 1996). The use of the 3' RACE system successfully isolated and characterized the 3' encoding and untranslated regions.

A large hydrophilic region is noticeable in the area of amino acid 530 of the human acid β-galactosidase, which is proposed as the site of proteolytic cleavage (Morreau et al., 1991; Yamamoto et al., 1990). The present study also show a large hydrophilic region in the area of amino acids 528–547, which very closely aligns with a region similar in hydrophilic properties of amino acid sequence in the human. This finding is similar to other reports and could also serve as the site of proteolytic cleavage in the dog (Ahern-Rindell et al., 1996).

EXAMPLE 17

Genotyping Screening of PW Dogs for Carriers of $G_{M1}$-gangliosidosis.

Genotyping performed on DNA from affected Portuguese Water dogs with $G_{M1}$-gangliosidosis revealed homozygosity for the R60H mutation. Genotype analysis was performed on the affected, carrier and normal Portuguese Water dogs with assignments of clinical status previously established based on the results of enzyme assay. Of 115 Portuguese Water dog samples analyzed, the data on mutation analysis are basically in concordance with that of the enzyme assay. All of the affected and carrier Portuguese Water dogs were found to be homozygous and heterozygous for the R60H mutation, respectively. Mutation analysis clarified the status of eight Portuguese Water dogs with enzyme activity ratios in the borderline or inconclusive range. None of the Portuguese Water dogs with normal acid β-galactosidase activity carried the R60H mutation.

These findings are consistent with a founder effect, as expected for a highly inbred animal. The present data confirm the expectation, based on Northern blot analysis (Ahern-Rindell et al., 1996), that the mutation causing $G_{M1}$-gangliosidosis in Portuguese Water dogs was likely the result of a change within the coding sequence of the dog β-galactosidase gene. An investigation was also made of whether the R60H mutation is responsible for $G_{M1}$-gangliosidosis in English Springer Spaniels (ESS) dogs. However, the R60H mutation was not found to be present in the ESS dog with $G_{M1}$-gangliosidosis. This suggests that the mutations causing $G_{M1}$-gangliosidosis in these two dog breeds are different, and may explain the differences in clinical, biochemical, and histochemical profiles (Ahern-Rindell et al., 1996) between the two breeds.

The availability of the full-length cDNA for the Portuguese Water dog acid β-galactosidase enables identification of the molecular defect in Portuguese Water dogs with $G_{M1}$-gangliosidosis, and will permit accurate carrier screening for the purposes of suitable breeding. Genomic analysis with PCR amplification and restriction enzyme digestion is a rapid and easy method for analysis of the normal and mutant alleles. Furthermore, the stability of DNA isolated from whole blood transported at room temperature enables facile shipping and handling of specimens. The fact that a single mutation (R60H) accounts for disease in all affected Portuguese Water dogs with $G_{M1}$-gangliosidosis also simplifies genetic testing for carrier identification and breeding purposes. Inconclusive results obtained with enzyme assay in some of the Portuguese Water dogs tested lead to ambiguity in determination of carrier or non-carrier status, and justify the preferential use of mutation analysis in screening for carriers in the Portuguese Water dogs.

EXAMPLE 18
Relationship of $G_{M1}$-gangliosidosis in PW Dogs to the Human Disease The Portuguese Water dogs with $G_{M1}$-gangliosidosis have features similar to the human infantile and juvenile forms of this disorder, with pathological features characterized by a lack of myelination due to primary failure or retardation of myelin development (Kaye et al., 1992). The availability of the full-length cDNA for the Portuguese Water dog acid β-galactosidase enables identification of the molecular defect in Portuguese Water dogs with $G_{M1}$-gangliosidosis, and will permit accurate carrier screening for the purposes of suitable breeding. In addition, Portuguese Water dog $G_{M1}$-gangliosidosis provides an animal model for the study of the molecular mechanisms of $G_{M1}$-gangliosidosis and other lysosomal storage diseases.

The following references were cited herein:

Ahern-Rindell, et al., (1996). Comparison of the canine and human acid β-galactosidase gene. Am. J.Med. Genet. 63: 340–345.

Alroy, et al., (1985). Neurovisceral and skeletal $G_{M1}$-gangliosidosis in dogs with β-galactosidase deficiency. Science 229:470–472.

Alroy, et al., (1992). Canine $G_{M1}$-gangliosidosis. A clinical, morphologic, histochemical, and biochemical comparison of two different models. Am. J Pathol. 140:675–689.

Hotumisligil, et al., (1993). Purification and immunological characterization of acid β-galactosidase from dog liver. Comp. Biochem. Physiol. 1068:373–382.

Ishii, et al., (1995). Clinical and molecular analysis of a Japanese boy with Morquio B disease. Clin Genet 48: 103–108.

Kaye, et al., (1992). Dysmyelinogenesis in animal model of $G_{M1}$-gangliosidosis. Pediatr. Neurol. 8: 255–261.

Kaye, et al., (1997). β-galactosidase gene mutations in patients with slowly progressive $G_{M1}$-gangliosidosis. J Child Neurol. 12: 242–247.

Kolodny, et al., (1976). Human leukocyte acid hydrolases: characterization of eleven lysosomal enzymes and study of reaction conditions for their automated analysis. Clinica Chimica Acta 70:247–257.

Morreau, et al., (1991). Organization of the gene encoding human lysosomal β-galactosidase. DNA and Cell Biology 10: 495–504.

Nanba, et al., (1990). Molecular cloning of mouse acid β-galactosidase cDNA: sequence, expression of catalytic activity and comparison with the human enzyme. Biochem. Biophys. Res. Commun. 173: 141–148.

Nanba, et al., (1991). Organization of the mouse acid β-galactosidase gene. Biochem. Biophys. Res. Commun. 178: 158–164.

Nishimoto et al., (1991). $G_{M1}$-gangliosidosis (β-galactosidase deficiency): identification of four mutations in different clinical phenotypes among Japanese patients. Am. J. Hum. Genet. 49: 566–574.

Oshma, et al., (1988). Cloning, sequencing, and expression of cDNA for human β-galactosidase. Biochem. Biophys. Res. Commun. 157:238–244.

Oshima, et al., (1991). Human β-galactosidase gene mutations in Morquio B disease. Am. J. Hum. Genet. 49: 1091–1093.

Oshima, et al., (1992). $G_{M1}$-gangliosidosis: tandem duplication within exon 3 of β-galactosidase gene in an infantile patient. Clin. Genet. 41: 235–238.

Read, et al., (1976). Neuronal-visceral $G_{M1}$-gangliosidosis in dogs with β-galactosidase deficiency. Science 194: 442.

Rittmann, et al., (1980). Dog $G_{M1}$-gangliosidosis: Characterization of the residual liver acid galactosidase. Am. J Hum. Genet. 32: 880.

Rodriguez, et al., (1982). Canine $G_{M1}$-gangliosidosis. An ultrastructural and biochemical study. J Neuropathol. Exp. Neurol. 41: 618–629.

Saunders, et al.,. (1988). $G_{M1}$-gangliosidosis in Portuguese Water dogs: pathologic and biochemical findings. Vet. Pathol. 25: 265–269.

Shell, et al., (1989). Neuronal-visceral $G_{M1}$-gangliosidosis in Portuguese Water dogs. J Vet. Intern Med. 3:1–7.

Suzuki, et al., (1995). β-galactosidase deficiency (β-galactosidosis): $G_{M1}$-gangliosidosis and Morquio B disease, in Scriver et al., (eds): The Metabolic and Molecular Bases of Inherited Disease, Vol 2, New York, McGraw-Hill, pp2785–2823.

Von Heijne, G. (1983). Patterns of amino acids near signal-sequence cleavage sites. Eur. J. Biochem. 133: 17–21.

Watson, M. E. E. (1984). Compilation of published signal sequences. Nucleic Acids Res. 12: 5145–5164.

Werner, et al., (1999). Anchoring of canine linkage groups with chromosome-specific markers. Mammalian Genome 10: 814–823.

Yamamoto, et al., (1990). Isolation, characterization, and mapping of a human acid β-galactosidase cDNA. DNA and Cell Biology 9: 119–127.

Yoshida, et al., (1991). Human β-galactosidase gene mutations in $G_{M1}$-gangliosidosis: a common mutation among Japanese adult/chronic cases. Am. J. Hum. Genet. 49: 435–442.

Yoshida, et al., (1992). $G_{M1}$-gangliosidosis adults: clinical and molecular analysis of 16 Japanese patients. Ann Neurol. 31: 328–332.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An isolated full lenght cDNA molecule encoding a canine acid β-galactosidase and having a sequence of SEQ ID No. 1.

2. A plasmid containing the isolated DNA molecule of claim 1, wherein said plasmid encodes canine acid β-galactosidase and regulatory elements necessary for expression of said protein in a cell.

3. The DNA molecule of claim 1 containing a mutation wherein nucleotide $G^{200}$ is substituted with A.

4. The DNA of claim 3, wherein said mutation is designated R60H.

5. An oligonucleotide having a sequence selected from the group consisting of SEQ ID Nos. 21 and 22.

6. A kit comprising:

a) reagents for isolation of genomic DNA;

b). oligonucleotides selected from the group consisting of SEQ ID No. 21 and SEQ ID No. 22;

c). reagents for PCR amplification; and, d). PmlI restriction endonuclease.

* * * * *

SEQUENCE LISTING

<160> NUMBER OF SEQ ID NOS: 25

<210> SEQ ID NO 1
<211> LENGTH: 2322
<212> TYPE: DNA
<213> ORGANISM: Canis familiaris
<220> FEATURE:
<221> NAME/KEY: CDS
<222> LOCATION: 22..2028
<223> OTHER INFORMATION: Contains coding sequence for Portuguese Water
      dog (-Galactosidase.  A g200 to a200 substitution mutation
      is present in the allele for Portuguese Water dog
      GM1-Gangliosidosis.

<400> SEQUENCE: 1
gggagggacg tggcgacggc gatggcgcgg cccgcggcgg ttcgcgtgct ctgggcgctg      60
ctgctgccgc tgctgctggg ctctgcgcgc ggcctgcgga atgcttccca gaggacattc     120
acaattgact acagccacaa ccgcttcctg aaggacggcc agcccttccg ctacatttcg     180
ggaagcattc actattcccg cgtgccccgc ttctactgga aggaccggct gctgaagatg     240
aagatggctg ggctgaatgc catccagacg tacgtgccct ggaactttca cgaacccag      300 ccgggacagt accagttttc tggggagcag gatgtgaatt attttattaa gctggcccat     360
gagctgggac tgctggtcat cctgaggccg ggaccctata tctgtgcaga gtgggacatg     420
ggaggattac ctgcttggct attattaaaa gaatctatta ttctccgttc ttctgatcca     480
gattaccttg cagctgtgga caaatggttg ggagtcctcc tgcccaagat gaagcctctc     540
ctctatcaga acggagggcc gattataacc atgcaggttg aaaatgaata tggcagctac     600
tttacctgcg attatgacta cctgcgtttc ctgcagaagc tcttccacca ccacctgggc     660
aatgatgtac ttctgttcac cactgatggg gcaaatgaaa agtttctgca gtgcggggct     720
ctgcagggcc tctatgccac agtggacttt ggaccaggtg ccaacatcac tgctgctttc     780
caaatccaga gaaagagtga gcccaaagga ccattggtga attctgaatt ctataccggc     840
tggttggatc attggggcca gccacactca acagtgagga ctgaagtggt ggcttcctcc     900
ctccatgata tacttgccca tggggcaaat gtgaacttgt acatgttcat aggtgggacc     960
aattttgcct attggaatgg ggccaacatg ccctaccaag cacagcccac cagttacgac    1020
tatgatgccc cactgagcga ggcaggggac ctcactgaga agtattttgc tctgcgagaa    1080
gttattcgga agtttgaaaa agtaccagaa ggttttatcc ctccgtctac acccaagttt    1140
gcatatggaa aagttgctct gaagaagtta aagacggtgg aggaggccct gaatgttctg    1200
tgtccgcctg ggcccataaa cagcctttat cccttgacgt ttatccaggt gaaacagtat    1260
ttcggttttg tgatgtaccg aacaacactt cctcaagact gcagtgaccc cacaccctg    1320 tcttcacccc tcagtggagt ccacgaccgc gcctatgtct ctgtggatgg ggtgcccag    1380 ggagtcatgg agcgaagtaa tgtcatcact ctgaacataa ccgggaaggc tggagccact    1440
ctggacctgc tggtggagaa catgggacgt gtgaactatg cagatatat caatgatttt    1500 aagggcctta tttctaacct gaccccttggg tccagtatcc tcacaaactg gatgatcttc    1560
ccgttgaaca ctgaggatgc agtacgcagc cacctgggag gctggcatgg ccctaacaat    1620
ggccgccatg ataaaacctt tgcccaccgc tcgtctaact acacgctccc ggcctttat    1680 atggggaact ctctattccc cagtgggatc ccagacttgc cccaggacac ctttatccag    1740
tttcctggat ggaccaaggg tcaggtgtgg attaatggct ttaacctcgg tcgatattgg    1800

```
ccagcacggg gcccccagat gactttgttt gtgccacggc acatcctggt gacatcaacc    1860
ccaaacacca tcatggtgct ggaactggag cacgcgccct gtggtgacag tggcccagaa    1920
gtgtgcaccg tggagtttgt ggacaggccg gttatcggtg cccctccaac ccctggtcat    1980 cccctccag acctgtccca tcgagacttg agactggact atgtctgatg atgaaacact    2040
gtgacccgtt ggagtttcag ccttgcacgt acatcaccta tccccctgtg taatgccaac    2100
actcactgga aagttcaact ggaaaataga tttagagtgt gcattttctc ctgaggtttc    2160
caggcagcct ggtagtgccc aagcctccac tggcaggggc caccatgaat gcatgatgag    2220
ggcagtggca cacagtttgg aatggaagct ttgaaggtgt tcctgatttt tatttggag    2280 gaatcatgtt gtctttctgt taaataaaat ttgtattcaa at                      2322
```

<210> SEQ ID NO 2
<211> LENGTH: 668
<212> TYPE: PRT
<213> ORGANISM: Canis familiaris
<220> FEATURE:
<221> NAME/KEY: MUTATION
<222> LOCATION: 60
<223> OTHER INFORMATION: Arg to His mutation in R60H allele.
<223> OTHER INFORMATION: Portuguese Water dog (-Galactosidase Protein

<400> SEQUENCE: 2

```
Met Ala Arg Pro Ala Ala Val Arg Val Leu Trp Ala Leu Leu Leu
              5                  10                  15

Pro Leu Leu Leu Gly Ser Ala Arg Gly Leu Arg Asn Ala Ser Gln
             20                  15                  30

Arg Thr Phe Thr Ile Asp Tyr Ser His Asn Arg Phe Leu Lys Asp
             35                  40                  45

Gly Gln Pro Phe Arg Tyr Ile Ser Gly Ser Ile His Tyr Ser Arg
             50                  55                  60

Val Pro Arg Phe Tyr Trp Lys Asp Arg Leu Leu Lys Met Lys Met
             65                  70                  75

Ala Gly Leu Asn Ala Ile Gln Thr Tyr Val Pro Trp Asn Phe His
             80                  85                  90

Glu Pro Gln Pro Gly Gln Tyr Gln Phe Ser Gly Glu Gln Asp Val
             95                 100                 105

Glu Tyr Phe Ile Lys Leu Ala His Glu Leu Gly Leu Leu Val Ile
            110                 115                 120

Leu Arg Pro Gly Pro Tyr Ile Cys Ala Glu Trp Asp Met Gly Gly
            125                 130                 135

Leu Pro Ala Trp Leu Leu Leu Lys Glu Ser Ile Ile Leu Arg Ser
            140                 145                 150

Ser Asp Pro Asp Tyr Leu Ala Ala Val Asp Lys Trp Leu Gly Val
            155                 160                 165

Leu Leu Pro Lys Met Lys Pro Leu Leu Tyr Gln Asn Gly Gly Pro
            170                 175                 180

Ile Ile Thr Met Gln Val Glu Asn Glu Tyr Gly Ser Tyr Phe Thr
            185                 190                 195

Cys Asp Tyr Asp Tyr Leu Arg Phe Leu Gln Lys Leu Phe His His
            200                 205                 210

His Leu Gly Asn Asp Val Leu Leu Phe Thr Thr Asp Gly Ala Asn
            215                 220                 225

Glu Lys Phe Leu Gln Cys Gly Ala Leu Gln Gly Leu Tyr Ala Thr
            230                 235                 240
```

-continued

```
Val Asp Phe Gly Pro Gly Ala Asn Ile Thr Ala Ala Phe Gln Ile
                245                 250                 255

Gln Arg Lys Ser Glu Pro Lys Gly Pro Leu Val Asn Ser Glu Phe
                260                 265                 270

Tyr Thr Gly Trp Leu Asp His Trp Gly Gln Pro His Ser Thr Val
                275                 280                 285

Arg Thr Glu Val Val Ala Ser Ser Leu His Asp Ile Leu Ala His
                290                 295                 300

Gly Ala Asn Val Asn Leu Tyr Met Phe Ile Gly Gly Thr Asn Phe
                305                 310                 315

Ala Tyr Trp Asn Gly Ala Asn Met Pro Tyr Gln Ala Gln Pro Thr
                320                 325                 330

Ser Tyr Asp Tyr Asp Ala Pro Leu Ser Glu Ala Gly Asp Leu Thr
                335                 340                 345

Glu Lys Tyr Phe Ala Leu Arg Glu Val Ile Arg Lys Phe Glu Lys
                350                 355                 360

Val Pro Glu Gly Phe Ile Pro Pro Ser Thr Pro Lys Phe Ala Tyr
                365                 370                 375

Gly Lys Val Ala Leu Lys Lys Leu Lys Thr Val Glu Glu Ala Leu
                380                 385                 390

Asn Val Leu Cys Pro Pro Gly Pro Ile Asn Ser Leu Tyr Pro Leu
                395                 400                 405

Thr Phe Ile Gln Val Lys Gln Tyr Phe Gly Phe Val Met Tyr Arg
                410                 415                 420

Thr Thr Leu Pro Gln Asp Cys Ser Asp Pro Thr Pro Leu Ser Ser
                425                 430                 435

Pro Leu Ser Gly Val His Asp Arg Ala Tyr Val Ser Val Asp Gly
                440                 445                 450

Val Pro Gln Gly Val Met Glu Arg Ser Asn Val Ile Thr Leu Asn
                455                 460                 465

Ile Thr Gly Lys Ala Gly Ala Thr Leu Asp Leu Leu Val Glu Asn
                470                 475                 480

Met Gly Arg Val Asn Tyr Gly Arg Tyr Ile Asn Asp Phe Lys Gly
                485                 490                 495

Leu Ile Ser Asn Leu Thr Leu Gly Ser Ser Ile Leu Thr Asn Trp
                500                 505                 510

Met Ile Phe Pro Leu Asn Thr Glu Asp Ala Val Arg Ser His Leu
                515                 520                 525

Gly Gly Trp His Gly Pro Asn Asn Gly Arg His Asp Lys Thr Phe
                530                 535                 540

Ala His Arg Ser Ser Asn Tyr Thr Leu Pro Ala Phe Tyr Met Gly
                545                 550                 555

Asn Phe Ser Ile Pro Ser Gly Ile Pro Asp Leu Pro Gln Asp Thr
                560                 565                 570

Phe Ile Gln Phe Pro Gly Trp Thr Lys Gly Gln Val Trp Ile Asn
                575                 580                 585

Gly Phe Asn Leu Gly Arg Tyr Trp Pro Ala Arg Gly Pro Gln Met
                590                 595                 600

Thr Leu Phe Val Pro Arg His Ile Leu Val Thr Ser Thr Pro Asn
                605                 610                 615

Thr Ile Met Val Leu Glu Leu Glu His Ala Pro Cys Gly Asp Ser
                620                 625                 630

Gly Pro Glu Val Cys Thr Val Glu Phe Val Asp Arg Pro Val Ile
```

-continued

```
                                    635                 640                 645
Gly Ala Pro Pro Thr Pro Gly His Pro Pro Pro Asp Leu Ser His
            650                 655                 660
Arg Asp Leu Arg Leu Asp Tyr Val
            665

<210> SEQ ID NO 3
<211> LENGTH: 6
<212> TYPE: DNA
<213> ORGANISM: Unknown
<220> FEATURE:
<221> NAME/KEY: polyA_signal
<222> LOCATION: 1..6
<223> OTHER INFORMATION: eukaryotic polyadenylation signal

<400> SEQUENCE: 3 aataaa                                                                    6

<210> SEQ ID NO 4
<211> LENGTH: 42
<212> TYPE: DNA
<213> ORGANISM: Canis familiaris
<220> FEATURE:
<221> NAME/KEY: mutation
<222> LOCATION: 17
<223> OTHER INFORMATION: Wild type sequence of Portuguese Water dog
      (-Galactosidase surrounding site of G to A transversion
      responsible for R60H allele

<400> SEQUENCE: 4
agcattcact attcccgcgt gccccgcttc tactggaagg ac                            42

<210> SEQ ID NO 5
<211> LENGTH: 42
<212> TYPE: DNA
<213> ORGANISM: Canis familiaris
<220> FEATURE:
<221> NAME/KEY:
<222> LOCATION: 17
<223> OTHER INFORMATION: Sequence of R60H allele of Portuguese Water dog
      (-Galactosidase cDNA.  Position 17 is site of G to A
      transversion responsible for Arg to His amino acid
      substitution.

<400> SEQUENCE: 5
agcattcact attcccacgt gccccgcttc tactggaagg ac                            42

<210> SEQ ID NO 6
<211> LENGTH: 21
<212> TYPE: DNA
<213> ORGANISM: Artificial Sequence
<220> FEATURE:
<223> OTHER INFORMATION: 1 Forward: Synthetic oligonucleotide used with
      SEQ ID No. 7 (1 Reverse) for PCR amplification of
      nucleotides 118-444 of canine acid (-galactosidase cDNA
      (SEQ ID No. 1).

<400> SEQUENCE: 6
ttcacaattg actacagcca c                                                   21

<210> SEQ ID NO 7
<211> LENGTH: 20
<212> TYPE: DNA
<213> ORGANISM: Artificial Sequence
<220> FEATURE:
<223> OTHER INFORMATION: 1 Reverse: Synthetic oligonucleotide used with
      SEQ ID No. 6 (1 Forward) for PCR amplification of nucleotides
      118-444 of canine acid (-galactosidase cDNA (SEQ ID No. 1).
```

-continued

Also used as a primer for DNA sequencing and in 5' RACE.

<400> SEQUENCE: 7
taatagccaa gcaggtaatc                                                    20

<210> SEQ ID NO 8
<211> LENGTH: 17
<212> TYPE: DNA
<213> ORGANISM: Artificial Sequence
<220> FEATURE:
<223> OTHER INFORMATION: 2 Forward: Synthetic oligonucleotide used with
      SEQ ID No. 9 (2 Reverse) for PCR amplification of nucleotides
      368-802 of canine acid (-galactosidase cDNA (SEQ ID No. 1).
      Also used as a primer for DNA sequencing.

<400> SEQUENCE: 8
gactgctggt catcctg                                                       17

<210> SEQ ID NO 9
<211> LENGTH: 22
<212> TYPE: DNA
<213> ORGANISM: Artificial Sequence
<220> FEATURE:
<223> OTHER INFORMATION: 2 Reverse: Synthetic oligonucleotide used with
      SEQ ID No. 8 (2 Forward) for PCR amplification of nucleotides
      368-802 of canine acid (-galactosidase cDNA (SEQ ID No. 1).
      Also used as a primer for DNA sequencing.

<400> SEQUENCE: 9
gctcactctt tctctggatt tg                                                 22

<210> SEQ ID NO 10
<211> LENGTH: 20
<212> TYPE: DNA
<213> ORGANISM: Artificial Sequence
<220> FEATURE:
<223> OTHER INFORMATION: 3 Forward: Synthetic oligonucleotide used with
      SEQ ID No. 11 (3 Reverse) for PCR amplification of nucleotides
      752-1185 of canine acid (-galactosidase cDNA (SEQ ID No. 1).
      Also used as a primer for DNA sequencing.

<400> SEQUENCE: 10
gaccaggtgc caacatcact                                                    20

<210> SEQ ID NO 11
<211> LENGTH: 20
<212> TYPE: DNA
<213> ORGANISM: Artificial Sequence
<220> FEATURE:
<223> OTHER INFORMATION: 3 Reverse: Synthetic oligonucleotide used with
      SEQ ID No. 10 (3 Forward) for PCR amplification of nucleotides
      752-1185 of canine acid (-galactosidase cDNA (SEQ ID No. 1).

<400> SEQUENCE: 11
ctcctccacc gtctttaact                                                    20

<210> SEQ ID NO 12
<211> LENGTH: 22
<212> TYPE: DNA
<213> ORGANISM: Artificial Sequence
<220> FEATURE:
<223> OTHER INFORMATION: 4 Forward: Synthetic oligonucleotide used with
      SEQ ID No. 13 (4 Reverse) for PCR amplification of nucleotides
      1112-1920 of canine acid (-galactosidase cDNA (SEQ ID
      No. 1). Also used as a primer for DNA sequencing.

<400> SEQUENCE: 12
gttttatccc tccgtctaca cc                                                 22

```
<210> SEQ ID NO 13
<211> LENGTH: 18
<212> TYPE: DNA
<213> ORGANISM: Artificial Sequence
<220> FEATURE:
<223> OTHER INFORMATION: 4 Reverse: Synthetic oligonucleotide used with
      SEQ ID No. 12 (4 Forward) for PCR amplification of nucleotides
      1112-1920  of canine acid (-galactosidase cDNA (SEQ ID
      No. 1).

<400> SEQUENCE: 13
ttctgggcca ctgtcacc                                                  18

<210> SEQ ID NO 14
<211> LENGTH: 37
<212> TYPE: DNA
<213> ORGANISM: Artificial Sequence
<220> FEATURE:
<223> OTHER INFORMATION: 5 Reverse:  Synthetic oligonucleotide used in
      both 5' RACE and 3' RACE of canine acid (-galactosidase gene.

<400> SEQUENCE: 14
ggccacgcgt cgactagtac tttttttttt tttttttt                            37

<210> SEQ ID NO 15
<211> LENGTH: 21
<212> TYPE: DNA
<213> ORGANISM: Artificial Sequence
<220> FEATURE:
<223> OTHER INFORMATION: 6 Reverse:  Synthetic oligonucleotide used for
      5' RACE of canine acid (-galactosidase gene.

<400> SEQUENCE: 15
catgtcccac tctgcacaga t                                              21

<210> SEQ ID NO 16
<211> LENGTH: 20
<212> TYPE: DNA
<213> ORGANISM: Artificial Sequence
<220> FEATURE:
<223> OTHER INFORMATION: 7 Forward: Synthetic oligonucleotide used for
      3' RACE of canine acid (-galactosidase.  Also used as a
      sequencing primer for canine acid (-galactosidase cDNA.

<400> SEQUENCE: 16
tgatcttccc gttgaacact                                                20

<210> SEQ ID NO 17
<211> LENGTH: 21
<212> TYPE: DNA
<213> ORGANISM: Artificial Sequence
<220> FEATURE:
<223> OTHER INFORMATION: 8 Forward: Used with SEQ ID No. 18 (8 Reverse)
      for PCR amplification of the 5' UTR of (-galactosidase from
      genomic DNA and with SEQ ID No 20 (9 Reverse) for
      amplification of the entire cDNA of (-galactosidase.

<400> SEQUENCE: 17
agggacgtgg cgacggcgat g                                              21

<210> SEQ ID NO 18
<211> LENGTH: 17
<212> TYPE: DNA
<213> ORGANISM: Artificial Sequence
<220> FEATURE:
<223> OTHER INFORMATION: 8 Reverse:  Synthetic oligonucleotide used with
      SEQ ID No. 17 for PCR amplification of the 5' UTR of canine
``` acid (-galactosidase from genomic DNA.

<400> SEQUENCE: 18
ccgcaggccg cgcgcag                                                      17

<210> SEQ ID NO 19
<211> LENGTH: 20
<212> TYPE: DNA
<213> ORGANISM: Artificial Sequence
<220> FEATURE:
<223> OTHER INFORMATION: 9 Forward: Synthetic oligonucleotide used with
      SEQ ID No. 20 for PCR amplification of the 3' UTR of canine
      acid (-galactosidase from genomic DNA.

<400> SEQUENCE: 19
caggtgtgga ttaatggctt                                                   20

<210> SEQ ID NO 20
<211> LENGTH: 23
<212> TYPE: DNA
<213> ORGANISM: Artificial Sequence
<220> FEATURE:
<223> OTHER INFORMATION: 9 Reverse:  Used with SEQ ID No. 19 (9 Forward)
      for PCR amplification of the 3' UTR of (-galactosidase from
      genomic DNA and with SEQ ID No 17 (8 Forward) for
      amplification of the entire cDNA of (-galactosidase.

<400> SEQUENCE: 20
actccaacgg gtcacagtgt ttc                                               23

<210> SEQ ID NO 21
<211> LENGTH: 21
<212> TYPE: DNA
<213> ORGANISM: Artificial Sequence
<220> FEATURE:
<223> OTHER INFORMATION: 10 Forward: Synthetic oligonucleotide used with
      SEQ ID No. 22 (10 Reverse) for PCR amplification of exon 2 of
      canine acid (-galactosidase cDNA from genomic DNA to
      screen for the R60H mutation by PmlI digestion.

<400> SEQUENCE: 21
cttgctctgc agaatgcttc c                                                 21

<210> SEQ ID NO 22
<211> LENGTH: 22
<212> TYPE: DNA
<213> ORGANISM: Artificial Sequence
<220> FEATURE:
<223> OTHER INFORMATION: 10 Reverse: Synthetic oligonucleotide used with
      SEQ ID No. 21 (10 Forward) for PCR amplification of exon 2 of
      canine acid (-galactosidase cDNA from genomic DNA to screen
      for the R60H mutation by PmlI digestion.

<400> SEQUENCE: 22
ccctcttact tacgtctgga tg                                                22

<210> SEQ ID NO 23
<211> LENGTH: 27
<212> TYPE: DNA
<213> ORGANISM: Artificial Sequence
<220> FEATURE:
<223> OTHER INFORMATION: 11 Forward : R60H mutagenic oligonucleotide.

<400> SEQUENCE: 23
attcactatt cccacgtgcc ccgcttc                                           27

<210> SEQ ID NO 24

```
<211> LENGTH: 28
<212> TYPE: DNA
<213> ORGANISM: Artificial Sequence
<220> FEATURE:
<223> OTHER INFORMATION: 12 Forward: Synthetic oligonucleotide
      corresponding to selection primer for R60H mutagenesis.

<400> SEQUENCE: 24
ctgtgactgg tgacgcgtca accaagtc                                    28

<210> SEQ ID NO 25
<211> LENGTH: 6
<212> TYPE: DNA
<213> ORGANISM: Unknown
<220> FEATURE:
<223> OTHER INFORMATION: Sequence of PmlI restriction endonuclease
      cleavage site

<400> SEQUENCE: 25 cacgtg                                                             6
```